US010022200B2

(12) United States Patent
Richmond (10) Patent No.: US 10,022,200 B2
(45) Date of Patent: Jul. 17, 2018

(54) MICROSURGICAL INSTRUMENT (71) Applicant: Peregrine Surgical Ltd., New Britain, PA (US)

(72) Inventor: Theodore Todd Richmond, Doylestown, PA (US)

(73) Assignee: PEREGRINE SURGICAL, LTD, New Britain, PA (US)

( * ) Notice: Subject to any disclaimer, the term of this patent is extended or adjusted under 35 U.S.C. 154(b) by 336 days.

(21) Appl. No.: 14/835,018

(22) Filed: Aug. 25, 2015

(65) Prior Publication Data

US 2016/0051335 A1   Feb. 25, 2016

Related U.S. Application Data (60) Provisional application No. 62/070,447, filed on Aug. 25, 2014.

(51) Int. Cl.
*A61B 90/00* (2016.01)
*A61B 90/30* (2016.01)

(52) U.S. Cl.
CPC .............. *A61B 90/30* (2016.02); *A61B 90/36* (2016.02); *A61B 2090/306* (2016.02)

(58) Field of Classification Search
CPC .... A61B 90/30; A61B 90/36; A61B 2090/306
See application file for complete search history.

(56) References Cited

U.S. PATENT DOCUMENTS

| | | | |
|---|---|---|---|
| 4,347,837 A | 9/1982 | Hosono | |
| 4,674,497 A | 6/1987 | Ogasawara | |
| 4,744,360 A | 5/1988 | Bath | |
| 4,984,563 A | 1/1991 | Renaud | |
| 5,156,604 A | 10/1992 | Hessel et al. | |
| 5,172,685 A | 12/1992 | Nudelman | |
| 5,281,214 A * | 1/1994 | Wilkins | A61B 18/24 606/13 |
| 5,300,061 A | 4/1994 | Easley et al. | |
| 5,323,766 A | 6/1994 | Uram | |
| 5,356,407 A | 10/1994 | Easley et al. | |

(Continued)

FOREIGN PATENT DOCUMENTS

WO   2007133267 A1   11/2007

OTHER PUBLICATIONS

VITRECTOMY+PHACO—Stellaris PC Procedural Packs Combined with AFI (Air Forced Infusion)—published Jan. 1, 2013. (1 page).

(Continued)

*Primary Examiner* — Eric S Gibson
(74) *Attorney, Agent, or Firm* — Volpe and Koenig, P.C.

(57) ABSTRACT

A microsurgical instrument for illuminating an interior site includes an optical fiber having a length between opposed proximal and distal ends, wherein the proximal end of the optical fiber is configured for operative engagement with an illumination light source, the distal end of the optical fiber including a light emitting portion, a preformed curved portion of the optical fiber proximate to the distal end, wherein the curved portion has a predetermined bend or curve, a flexible tubular sleeve enclosing at least a portion of the optical fiber, wherein the tubular sleeve has a preformed curved portion corresponding to the curved portion of the optical fiber.

18 Claims, 8 Drawing Sheets

(56) References Cited

U.S. PATENT DOCUMENTS

| | | | |
|---|---|---|---|
| 5,372,585 A | | 12/1994 | Tiefenbrun et al. |
| 5,469,524 A | | 11/1995 | Esch et al. |
| 5,512,034 A | * | 4/1996 | Finn .................. A61B 1/00089 |
| | | | 600/138 |
| 5,520,222 A | | 5/1996 | Chikama |
| 5,549,565 A | | 8/1996 | Ryan et al. |
| 5,603,710 A | | 2/1997 | Easley et al. |
| 5,656,011 A | | 8/1997 | Uihlein et al. |
| 5,688,264 A | | 11/1997 | Ren et al. |
| 5,735,792 A | | 4/1998 | Vanden Hoek et al. |
| 5,741,225 A | | 4/1998 | Lax et al. |
| 5,766,164 A | | 6/1998 | Mueller et al. |
| 5,785,645 A | | 7/1998 | Scheller |
| 5,807,242 A | * | 9/1998 | Scheller ............. G02B 23/2453 |
| | | | 385/117 |
| 5,807,424 A | | 9/1998 | de Ruiter et al. |
| 5,855,577 A | | 1/1999 | Murphy-Chutorian et al. |
| 5,855,755 A | | 1/1999 | Murphy et al. |
| 5,865,831 A | | 2/1999 | Cozean et al. |
| 5,957,916 A | | 9/1999 | Jeevanandam et al. |
| 5,993,072 A | | 11/1999 | de Juan, Jr. et al. |
| RE36,473 E | | 12/1999 | Esch et al. |
| 6,015,403 A | | 1/2000 | Jones |
| 6,053,911 A | | 4/2000 | Ryan et al. |
| 6,129,721 A | | 10/2000 | Kataoka et al. |
| 6,142,990 A | | 11/2000 | Burk |
| 6,428,553 B1 | * | 8/2002 | Trese .................. A61F 9/00736 |
| | | | 606/16 |
| 6,572,608 B1 | * | 6/2003 | Lee ......................... A61F 9/008 |
| | | | 606/13 |
| 6,575,989 B1 | | 6/2003 | Scheller et al. |
| 6,984,230 B2 | * | 1/2006 | Scheller ................. A61B 18/22 |
| | | | 606/15 |
| 7,141,048 B1 | | 11/2006 | Charles |
| 7,402,158 B2 | * | 7/2008 | Scheller ................. A61B 18/22 |
| | | | 128/898 |
| 7,473,249 B2 | | 1/2009 | Scheller et al. |
| 7,766,904 B2 | * | 8/2010 | McGowan, Sr. ....... A61F 9/008 |
| | | | 606/13 |
| 7,842,027 B2 | | 11/2010 | Lieponis |
| 7,972,326 B2 | * | 7/2011 | Scheller ................. A61F 9/009 |
| | | | 606/13 |
| 8,075,553 B2 | * | 12/2011 | Scheller ................. A61B 18/22 |
| | | | 606/13 |
| 8,162,928 B2 | * | 4/2012 | Vijfvinkel ............ A61B 3/0008 |
| | | | 128/898 |
| 8,187,293 B2 | | 5/2012 | Kirchhevel |
| 9,770,363 B2 | * | 9/2017 | Scheller .............. A61F 9/00821 |
| 9,775,745 B2 | * | 10/2017 | Scheller .............. A61F 9/00823 |
| 9,795,510 B2 | * | 10/2017 | Scheller .............. A61F 9/00821 |
| 2003/0088257 A1 | * | 5/2003 | Awh ........................ A61F 9/007 |
| | | | 606/161 |
| 2003/0191461 A1 | * | 10/2003 | Scheller ................. A61B 18/22 |
| | | | 606/15 |
| 2005/0154379 A1 | * | 7/2005 | McGowan, Sr. ....... A61F 9/008 |
| | | | 606/4 |
| 2006/0173448 A1 | | 8/2006 | Scheller et al. |
| 2006/0184162 A1 | * | 8/2006 | Smith ..................... A61F 9/007 |
| | | | 606/4 |
| 2007/0239149 A1 | | 10/2007 | Lieponis |
| 2007/0265602 A1 | | 11/2007 | Mordaunt et al. |
| 2008/0287938 A1 | * | 11/2008 | Scheller ................. A61B 18/22 |
| | | | 606/15 |
| 2012/0071727 A1 | * | 3/2012 | Hanson .................. A61B 17/24 |
| | | | 600/249 |
| 2012/0172851 A1 | | 7/2012 | Lee et al. |
| 2013/0090635 A1 | * | 4/2013 | Mansour .............. A61F 9/00821 |
| | | | 606/4 |
| 2013/0253387 A1 | * | 9/2013 | Bonutti .............. A61H 23/0245 |
| | | | 601/46 |
| 2014/0074079 A1 | * | 3/2014 | Scheller .............. A61F 9/00821 |
| | | | 606/16 |
| 2015/0038790 A1 | * | 2/2015 | Rontal ..................... A61B 1/233 |
| | | | 600/158 |
| 2015/0164314 A1 | * | 6/2015 | Peterson .............. A61B 3/0008 |
| | | | 600/249 |
| 2016/0051335 A1 | * | 2/2016 | Richmond ......... A61B 19/5202 |
| | | | 600/249 |
| 2016/0287348 A1 | * | 10/2016 | Vayser .................... A61B 90/30 |
| 2016/0302970 A1 | * | 10/2016 | Mansour ............. A61F 9/00821 |

OTHER PUBLICATIONS

Search Report and Written Opinion dated Nov. 30, 2015 received in the corresponding PCT Application (PCT/US15/48893).

Communication Pursuant to Rule 164(1) in counterpart European Application No. 15836723.5, dated Mar. 14, 2018, with a Supplemental Partial European Search Report and Provisional Opinion.

\* cited by examiner

FIG.6B though is itself not occupied by the optical fiber distal end which extends therefrom...

MICROSURGICAL INSTRUMENT

CROSS REFERENCE TO RELATED APPLICATION

This application claims the benefit of U.S. Provisional Application 62/070,447 filed on Aug. 25, 2014, which is incorporated by reference as if fully set forth.

FIELD OF INVENTION

The present invention relates generally to medical devices, and more particularly to a microsurgical instrument.

BACKGROUND

In ophthalmic surgery, adequate visualization of interior portions of the eye is critical to the success of the surgical procedure. The development of endoillumination has greatly improved the way surgeons are able to visualize the interior portions of the eye. One form, chandelier lighting, provides a stationary and dispersed form of light, which may be focused or diffused, from an anterior location. Most common ophthalmic surgery procedures involve making three stab incisions (i.e., sclerotomy) for accessing the eye through the vitreous chamber. One of these incisions is used for insertion of the illuminator. A second incision is ultimately used for insertion of an infusion cannula, which is used to introduce fluids to prevent collapse and otherwise maintain the integrity of the eye. A third incision is made in the eye for insertion of the specific surgical instruments to be used for performing the surgery. To minimize the invasiveness of this type of surgery, it is desirable to reduce the size of the incisions accommodating instruments ranging from 18 g to 42 g.

There are various types of illuminators employed in ophthalmic surgery. These illuminators typically employ an optical fiber having a flexible elongate length with opposed proximal and distal ends. The optical fiber is usually encased in an elongate tubular sleeve with some form of cladding. The proximal end of the optical fiber is secured to a connector adapted for coupling to a corresponding illumination light source for supplying the illumination light through the optical fiber. The distal end of the optical fiber is inserted through an incision in the eye and the illumination light emitted therefrom is dispersed throughout the vitreous chamber of the eye.

Some problems have been experienced with use of prior art illuminators. For example, the optical fiber and sleeve typically exhibits a relatively high degree of resistance to bending or stiffness. When the distal end of the optical fiber is inserted vertically into the eye, the collective weight of the remaining length of the optical fiber and sleeve is directed upon the distal end causing some degree of shear force. This weight generates a bending moment or torque on the optical fiber and sleeve and causes undue stress at the point of contact with the eye (i.e., incision) and potentially affecting the positioning and integrity of the eyeball itself.

Another problem involves the undesirable tendency of the distal end of the optical fiber where the light is emitted to inadvertently slide out from the eye during the surgical procedure. This requires halting of the surgery to re-insert the optical fiber, which can be problematic if the incision seals on its own and becomes not readily detectable or the optical fiber becomes contaminated.

Accordingly, there is a need for a microsurgical instrument adapted for providing illumination light that overcomes the problems discussed above. In particular, there is a need for a microsurgical instrument designed to reduce or minimize the bending moment on the site of a surgical incision. There is a further need to provide a microsurgical instrument configured for enhanced securement to the surgical incision, thereby substantially reducing the incidence of inadvertent slippage or withdrawal therefrom.

SUMMARY

The present invention relates generally to a microsurgical instrument for illuminating an interior site. In particular, the instrument of the present invention is configured for providing illumination of the interior portions of a body cavity, such as the vitreous chamber of the eye, during surgery. The instrument of the present invention provides an illuminating device having an optical fiber with a distal end for insertion into the eye via a surgical incision. The optical fiber is adapted for conveying light from a light source along the longitudinal axis to the distal end from which light is emitted therefrom. The instrument of the present invention can further be operated to selectively move the optical fiber distal end axially to a desired location in the eye. The resulting emitted light can be in the form of a focused light or a diffused light depending on the configuration of the optical fiber distal end.

The instrument of the present invention is designed to substantially reduce or minimize undesirable torque forces on the eye especially at the point of insertion, which can compromise the incision and the proper positioning of the eyeball itself during surgery. The instrument of the present invention further includes improved means to firmly secure the distal end of the optical fiber in the patient's eye, thus preventing or at least minimizing inadvertent displacement from the eye. The instrument of the present invention greatly reduces risks of complications to the patient's eye during surgery and inadvertent retraction of the distal end of the optical fiber from the eye for enhanced ease of use. Accordingly, the instrument of the present invention is characterized by improved safety and added convenience.

In one aspect of the present invention, there is provided a microsurgical instrument for illuminating an interior site, comprising:

an optical fiber having a length between opposed proximal and distal ends, the proximal end of the optical fiber being configured for operative engagement with an illumination light source;

the distal end of the optical fiber including a light emitting portion; and a preformed curved portion of the optical fiber proximate to the distal end, the curved portion having a predetermined bend or curve.

In another aspect of the present invention, there is provided a microsurgical instrument for illuminating an interior site, comprising:

an optical fiber having a length between opposed proximal and distal ends, the proximal end of the optical fiber being configured for operative engagement with an illumination light source;

the distal end of the optical fiber including a light emitting portion;

a flexible tubular sleeve enclosing at least a portion of the optical fiber; and a tubular fitting affixed to a distal end of the sleeve through which the distal end of the optical fiber passes therethrough, the tubular fitting being configured for coupling engagement with a cannula for rigidly securing the two together.

In a further aspect of the present invention, there is provided a microsurgical instrument for illuminating an interior site, comprising:

an optical fiber having a length between opposed proximal and distal ends, the proximal end of the optical fiber being configured for operative engagement with an illumination light source;

the distal end of the optical fiber including a light emitting portion;

a preformed curved portion of the optical fiber proximate to the distal end, the curved portion having a predetermined bend or curve;

a flexible tubular sleeve enclosing at least a portion of the optical fiber, the tubular sleeve having a preformed curved portion for maintaining the curved portion of the optical fiber; and a tubular fitting affixed to a distal end of the sleeve through which the distal end of the optical fiber passes therethrough, the tubular fitting being configured for coupling engagement within an interior portion of the cannula, thereby rigidly securing the two together.

BRIEF DESCRIPTION OF THE DRAWINGS

The following drawings are illustrative of preferred embodiments of the present invention, and are not intended to limit the invention as encompassed by the claims forming part of the application, wherein like items are identified by the same reference designations:

DETAILED DESCRIPTION OF THE PREFERRED EMBODIMENTS

The present invention is directed generally to a microsurgical instrument for illuminating an interior site. In particular, the instrument of the present invention is configured for providing illumination of the interior portions of a body cavity, such as the vitreous chamber of the eye, during surgery. The instrument of the present invention provides an illuminating device having an optical fiber with a distal end for insertion into the eye via a surgical incision. The optical fiber is adapted for conveying light from a light source along the longitudinal axis to the distal end from which light is emitted therefrom. The instrument of the present invention can further be operated to selectively move the optical fiber distal end axially to a desired location in the eye. The resulting emitted light can be in the form of a focused light or a diffused light depending on the configuration of the optical fiber distal end.

The instrument of the present invention is designed to substantially reduce or minimize undesirable torque forces on the eye especially at the point of insertion, which can compromise the incision and the proper positioning of the eyeball itself during surgery. The instrument of the present invention further includes improved means to firmly secure the distal end of the optical fiber in the patient's eye, thus preventing or at least minimizing inadvertent displacement from the eye. The instrument of the present invention greatly reduces risks of complications to the patient's eye during surgery and inadvertent retraction of the distal end of the optical fiber from the eye for enhanced ease of use. Accordingly, the instrument of the present invention is characterized by improved safety and added convenience.

In one embodiment of the present invention, there is provided a microsurgical instrument for illuminating an interior site, which includes an optical fiber having a length between opposed proximal and distal ends, where the proximal end of the optical fiber is configured for operative engagement with an illumination light source and the distal end of the optical fiber includes a light emitting portion, and a preformed curved portion of the optical fiber proximate to the distal end, where the curved portion has a predetermined bend or curve.

In a preferred embodiment of the present invention, the present instrument further includes a handpiece having a bore extending therethrough with the optical fiber extending through the handpiece bore, and an adjustable mechanism operatively associated with the handpiece. The adjustable mechanism is operatively engaged to the optical fiber for selectively moving the optical fiber backward and forward relative to the handpiece bore, thereby advancing and retracting the distal end of the optical fiber within the interior site.

Figure 1:
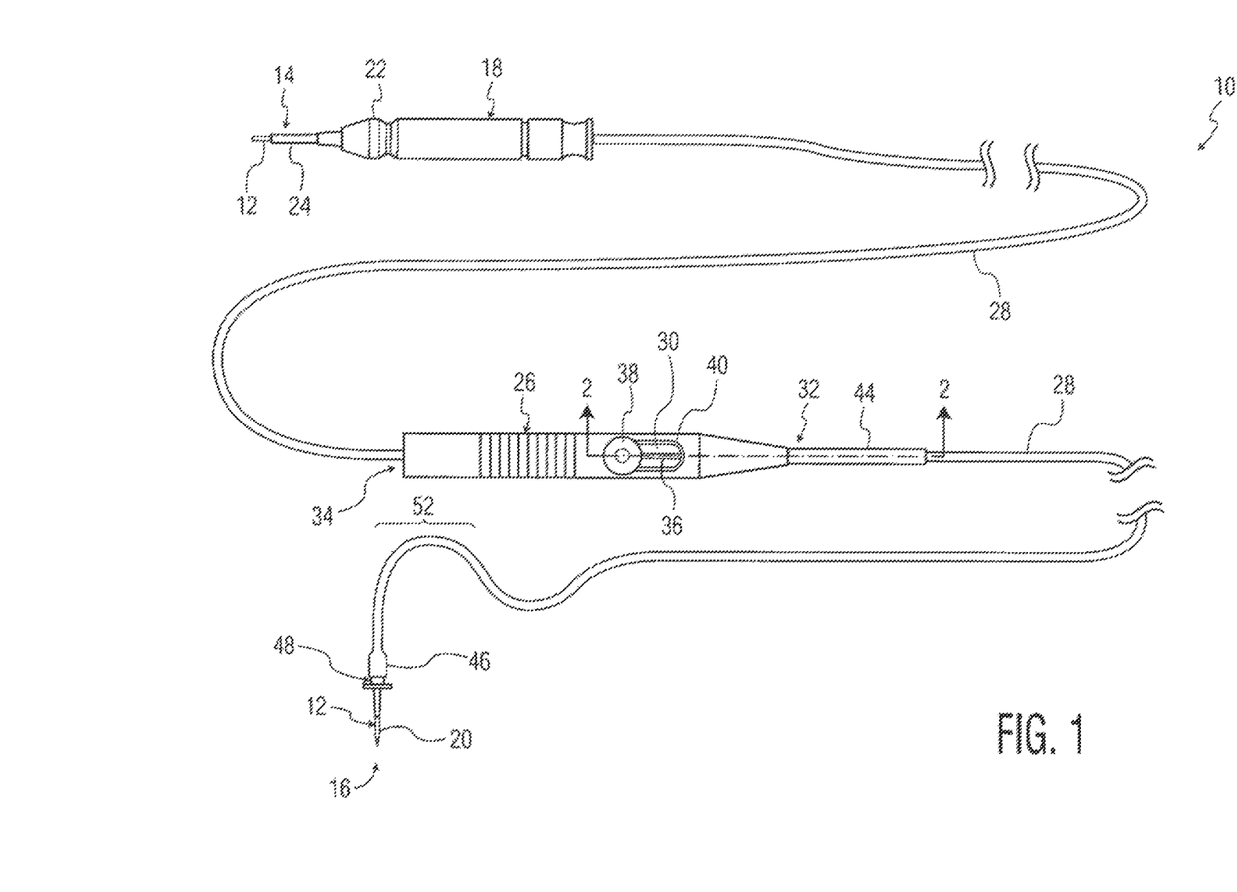
FIG. 1 is a pictorial view of a microsurgical instrument for illuminating an interior site in accordance with one embodiment of the present invention.

With reference to FIG. 1, there is shown a 'microsurgical instrument for illuminating an interior site (referred hereinafter as the "instrument") identified generally by reference numeral 10 in accordance with one embodiment of the present invention. The instrument 10 is suitable for use in a medical setting, and is especially suited for use in ophthalmic surgical procedures. The instrument 10 is configured for providing illumination of the interior portions of a body cavity, such as the vitreous chamber of the eye, during surgery. The instrument 10 is compact and lightweight for enhancing ease of use and portability, while remaining relatively simple and cost effective to make and implement.

Although the present invention as shown and described herein is used in connection with ophthalmic surgical procedures, it is understood that it is not meant to be limiting, and that the configuration and dimension of the present invention can readily be modified as required for a given application as recognized by those skilled in the art.

The instrument 10 generally includes an elongate length of optical fiber 12 having a proximal end 14 and an opposed distal end 16 with a light source connector 18 at the optical fiber proximal end 14. The optical fiber 12 may be composed of a suitable flexible, transparent fiber material, which may be selected from extruded glass (e.g., silica, fluoride, or phosphate) or plastic. A light emitting portion 20 is located at the optical fiber distal end 16 for emitting illumination light therefrom. The light emitting portion 20 may be suitably configured to emit any form of illumination lighting. In the present embodiment of the invention, the light emitting portion 20 includes a cone shaped taper for providing wide-angled illumination lighting. In the alternative embodiment of the invention, the light emitting portion 20 may include a cylinder shaped square end for providing focused illumination lighting.

The light source connector 18 includes a body 22 and a male connector portion 24 for plugging into a corresponding light source device (not shown). The exterior configuration of the connector body 22 is determined depending on the particular commercially available light source device with which the instrument 10 is to be used for easy attachment and removal from the light source device. Therefore, the particular exterior configuration of the light source connector 18 shown in drawing figures is illustrative only. In this manner, the instrument 10 of the present invention that is used with different types of light source devices will have a light source connector 18 with an exterior configuration that is adapted to removable attach the connector to the particular light source device.

Figure 3:
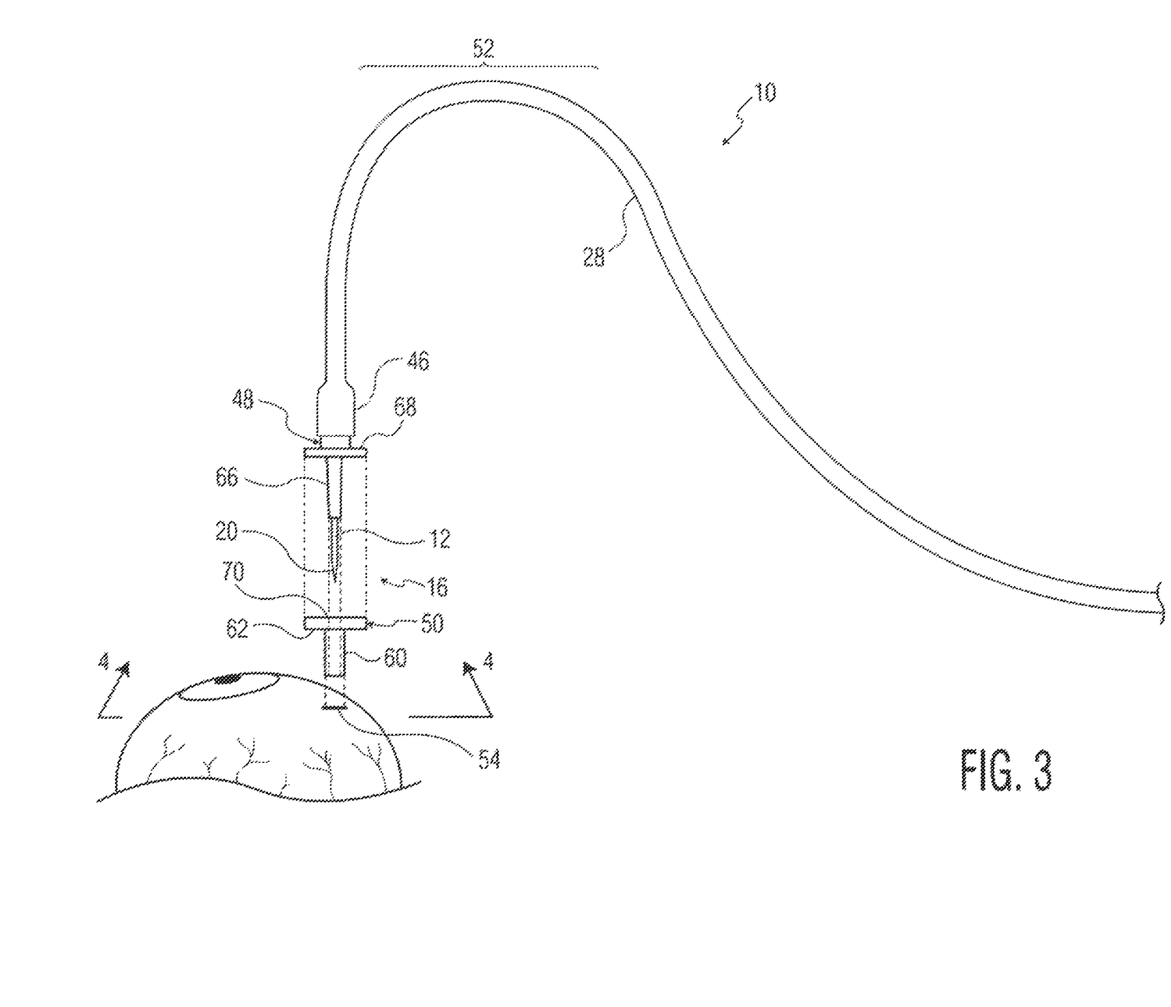
FIG. 3 is an exploded assembly view of a distal end of the microsurgical instrument shown in association with a patient's eye in accordance with the present invention.

The instrument 10 further includes a handpiece 26 located at an intermediate portion of the optical fiber 12, and a tubular jacket or sleeve 28 surrounding the length of the optical fiber 12 extending from the connector 18. The sleeve 28 may be composed of flexible, tubular plastic polymer material such as, for example, polyvinyl chloride (PVC). The sleeve 28 terminates at free end 46 through which the light emitting portion 20 extends therefrom (as shown in FIGS. 1 and 3). In one embodiment an epoxy is used to bond the connector 18 with the sleeve 28. An epoxy is applied between the surfaces of the connector 18 and the sleeve 28, is preferably allowed to cure for at least twelve hours. One of ordinary skill in the art recognizes that other methods for fixing the connector 18 with the sleeve 28 can be used. The sleeve free end 46 includes a tubular fitting 48 attached thereto through which the optical fiber 12 passes out to the exterior. The tubular fitting 48 may be composed of a metal material, a ceramic material, or a plastic polymer material, and suitably configured for proper rigid coupling with a cannula 50 (see FIGS. 3 and 4) as will be described hereinafter. The sleeve 28 and the optical fiber 12 further includes a preformed curved portion 52 disposed proximate the sleeve free end 46 and having a predetermined or preformed curvature. In one embodiment, the handpiece 26 is formed from an acetal, or a polyacetal of formaldehyde.

Figure 2:
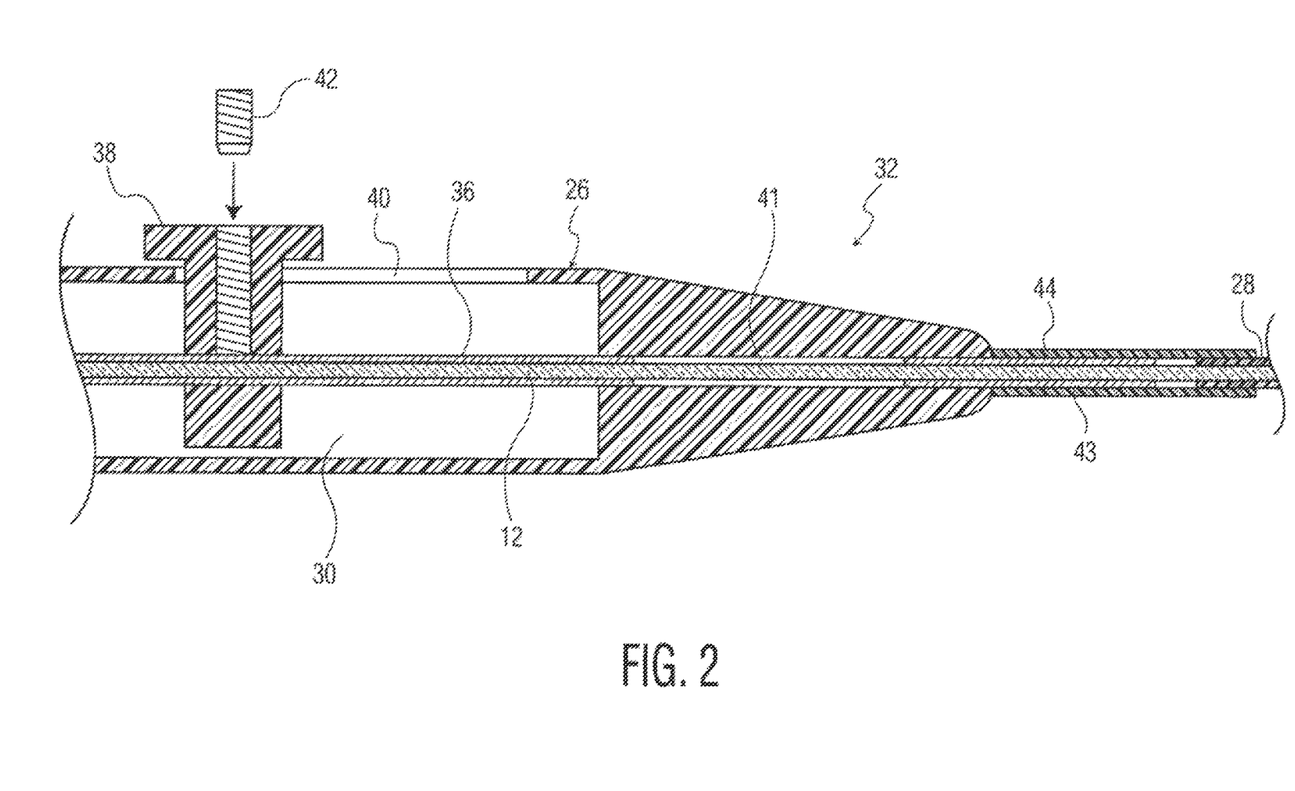
FIG. 2 is an enlarged cross-sectional view of the microsurgical instrument along lines 2-2 of FIG. 1 in accordance with the present invention.

The handpiece 26 is comprised of a bore 30 extending axially between a forward end 32 and a rearward end 34 thereof, and a tubular member 36 disposed coextensively with the handpiece bore 30. The handpiece 26 is operatively engaged to the optical fiber 12 for selectively extending and retracting the optical fiber 12 through the sleeve 28 and tubular fitting 48 as will be described hereinafter. A finger knob 38 extending from the bore 30 through slot 40 is affixed to the tubular member 36. In one embodiment, the tubular member 36 is a 20 gauge stainless steel tube. One of ordinary skill in the art recognizes that other types of material and other gauges can be used for the tubular member 36. The finger knob 38 can be moved selectively back and forth in a sliding action in the slot 40.

The light source connector 18, handpiece 26, tubular fitting 48 and cannula 50 are each preferably constructed from a suitable rigid, strong, durable material. Examples of such rigid, strong, durable material include, but are not limited to, plastic polymers, metals, laminates, composites, and the like. Preferably, the rigid, strong, durable material is a plastic polymer, and more preferably, a thermosetting plastic. Suitable plastic polymers include nylon, polyethylene, polypropylene, polyvinyl chloride, polyacrylate, and the like. Each of the components can be constructed using any suitable manufacturing processes as known to those skilled in the art, including, but not limited to, casting (e.g., centrifugal, continuous, die), molding (e.g., injection, compression, extrusion), forming (e.g., forging, rolling, extrusion, pressing), machining, and the like.

With reference to FIG. 2, a portion of the optical fiber 12 disposed within the bore 30 is securely retained by the tubular member 36. The tubular member 36 and optical fiber 12 is captively held by the finger knob 38 through suitable means such as, for example, an adhesive or a fastener. In the present embodiment of the invention, the tubular member 36 is affixed to the finger knob 38 via a set screw 42. The forward end 32 further defines a tip channel 41 through which the tubular member 36 slidingly engages at one end. A fixed rigid tubing 43 is mounted at the other end of the tip channel 41 with a portion extending therefrom. In one embodiment, the tip channel 41 is formed from stainless steel. A flexible collar 44 is provided to retain the extended portion of the rigid tubing 43 and an end portion of the sleeve 28 housing the optical fiber 12 therethrough. In this manner, the optical fiber 12 extending through the handpiece bore 30 passes into the sleeve 28 which is connected to the forward end 32 of the handpiece 26 via the flexible collar 44. The flexible collar 44 ensures line continuity of the optical fiber 12 between the joined portions of the handpiece 26 and the sleeve 28. In one embodiment, the optical fiber 12 is made from plastic, or a poly(methyl methacrylate) (PMMA), or acrylic. In one embodiment, the flexible collar 44 is formed from a polytetrafluoroethylene (PTFE) jacket with an etched surface. The etched surface provides an improved surface for bonding the flexible collar 44 with another component.

Figure 2A:
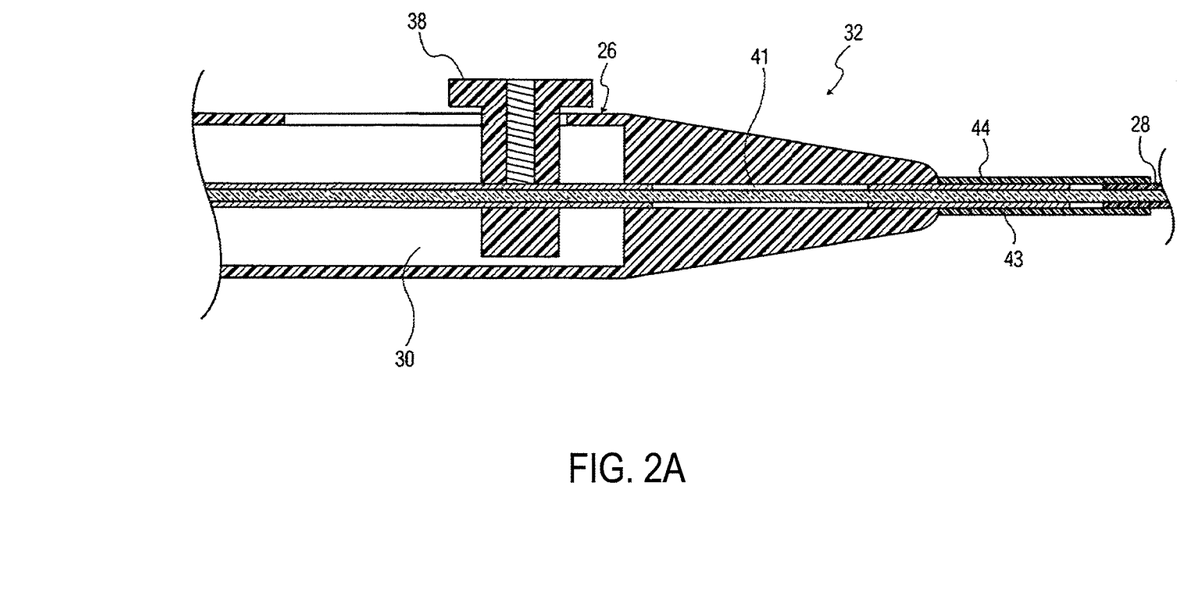
FIG. 2A is an enlarged cross-sectional view of the microsurgical instrument with a finger knob in the extended position.
Figure 6A:
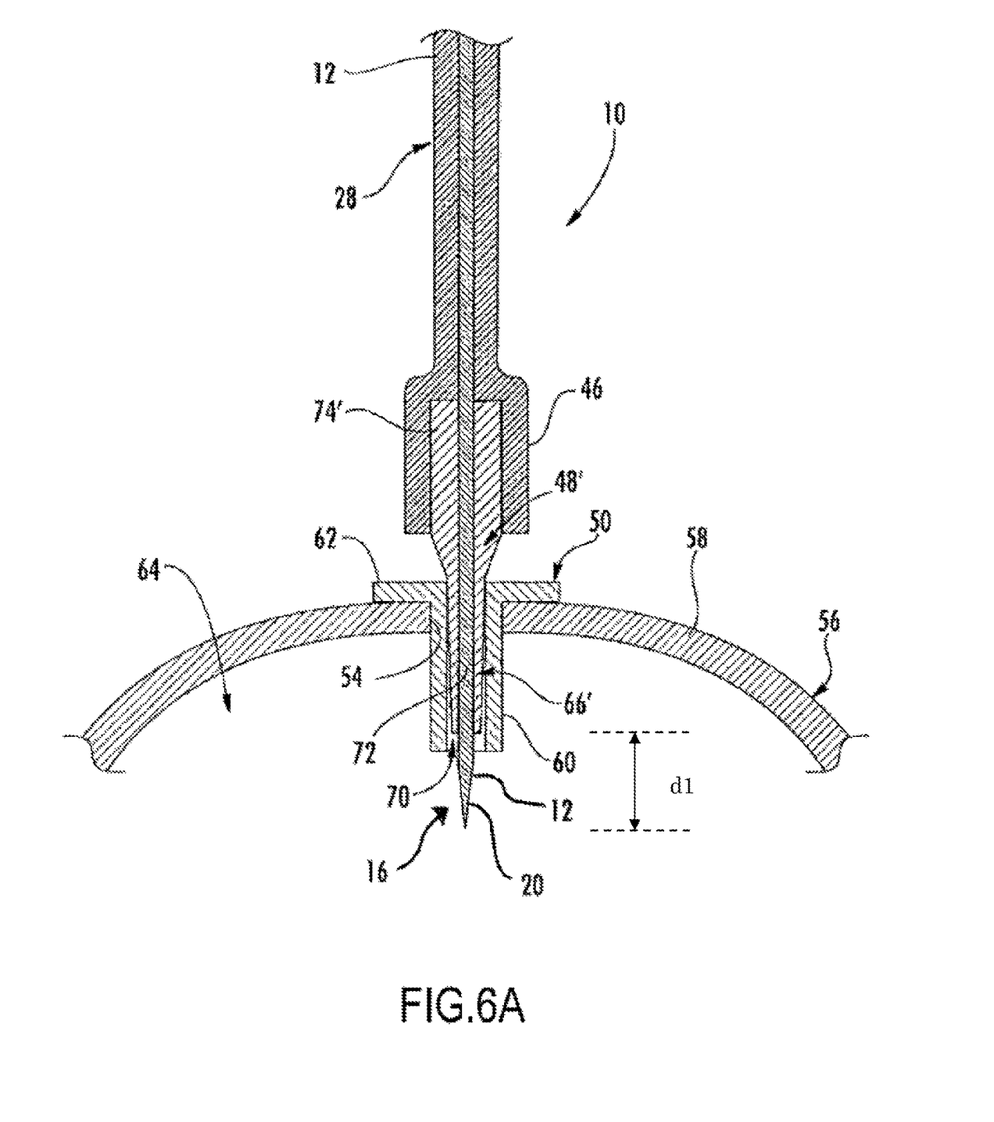
FIG. 6A is a detailed cross-sectional view of a tubular fitting of the microsurgical instrument according to another embodiment with an optical fiber in a retracted position.
Figure 6B:
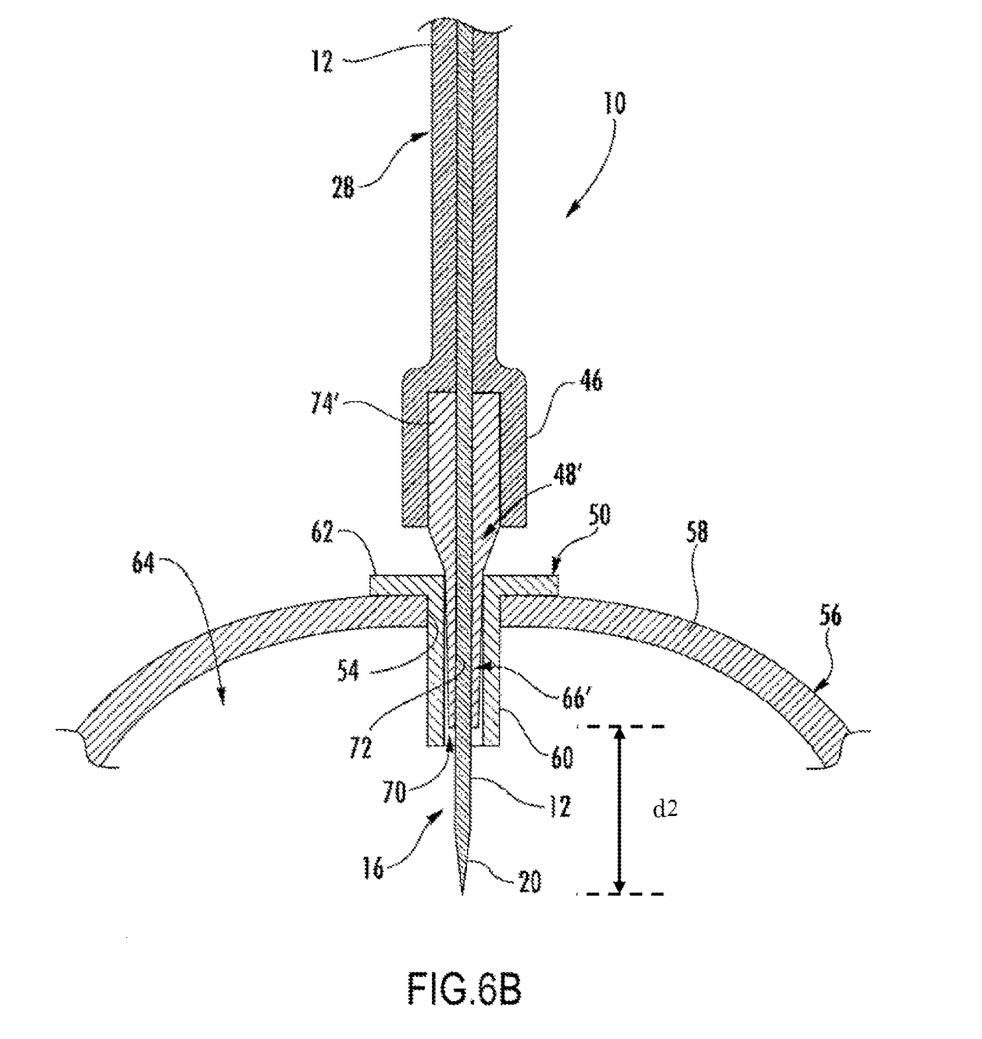
FIG. 6B is a detailed cross-sectional view of a tubular fitting of the microsurgical instrument according to another embodiment with an optical fiber in an extended position.

As shown in FIG. 2, the finger knob 38 and tubular member 36, in combination, provides an adjustment mechanism for selectively moving the optical fiber 12 through the sleeve 28. This is achieved by selectively moving the finger knob 38 back or forth in a sliding action in the slot 40. The finger knob 38 is moved toward the handpiece rearward end 34 for retracting the light emitting portion 20 of the optical fiber 12 rearward toward the sleeve 28 and tubular fitting 48. Alternately, the finger knob 38 is moved toward the handpiece forward end 32 for extending the light emitting portion 20 of the optical fiber 12 from the sleeve 28 and tubular fitting 48. FIG. 2 shows the finger knob 38 in a retracted position wherein the optical fiber 12 is retracted. The distance the optical fiber 12 extends from the tubular fitting 48 in the retracted position is shown as d1 in FIG. 6A. In a preferred embodiment, the optical fiber 12 extends beyond the tubular fitting 48 by 0.035" with a tolerance of +/−0.065" when the finger knob 38 is in the retracted position, i.e. the positions shown in FIG. 2 and FIG. 6A. The position of the optical fiber 12 in the retracted position with respect to the tubular fitting 48 is illustrated in FIG. 6A. FIG. 2A shows the finger knob 38 in another position which corresponds to an extended position for the optical fiber 12. The extended position of the optical fiber 12 is shown in FIG. 6B. In a preferred embodiment, the optical fiber 12 extends 0.285"

with a tolerance of +/−0.040" from the tubular fitting 48 when the finger knob 38 is in the extended position. The extension (d2) of the optical fiber 12 is illustrated and labeled in FIG. 6B from the tubular fitting 48 in the extended position. These minimum and maximum values for the amount of extension of the optical fiber 12 beyond the tubular fitting 48 are calibrated and set such that a surgeon, or other medical personnel, cannot exceed these limits. The minimum and maximum values of extension for the optical fiber are specifically selected to reduce the risk of the optical fiber 12 contacting the retina or other bodies within the eye. This arrangement provides a fixed stop so that the optical fiber 12 cannot exceed the calibrated, pre-set minimum and maximum extension values, which could result in a surgeon extending too much of the optical fiber 12, and functions as a safety feature. The movement of the finger knob 38 is limited by the ends of the bore 30, and the two end positions of the finger knob 38 within the bore 30 correspond to the extended and retracted position of the optical fiber 12 within the tubular fitting 48. In one embodiment, the optical fiber 12 extends beyond the tubular fitting 48 by an absolute maximum value of 1.25" when the finger knob 38 is in the extended position. This value is selected to prevent the optical fiber 12 from extending too deep into a patient's eye and causing damage to the patient's retina. In one embodiment, the optical fiber 12 extends between 0.015" to 0.055" from the tubular fitting 48 in the retracted position. In one embodiment, the optical fiber 12 extends 0.035" from the tubular fitting 48 in the retracted position. In another embodiment, the optical fiber extends between 0.20" to 0.45" from the tubular fitting 48 in the extended position. In one embodiment, the optical fiber 12 extends 0.285" from the tubular fitting 48 in the extended position. In another embodiment, the optical fiber 12 extends 1.25" from the tubular fitting 48 in the extended position.

In one embodiment, the finger knob 38 is formed from acetal plastic, or a polyacetal of formaldehyde. In one embodiment, the sleeve 28 is formed from PTFE. In one embodiment, the sleeve 28 includes a PTFE jacket with an etched surface. Due to PTFE's low coefficient of friction, the PTFE jacket of the sleeve 28 is etched to increase the coefficient of friction to improve the ability of the sleeve 28 to be bonded. The etching is preferably achieved by a fluoropolymer etching solution.

With reference to FIG. 3, the instrument 10 is shown in preparation for surgical insertion into a patient's eye 56. The light emitting portion 20 is introduced into the incision 54 which is frictionally retained in position. The preformed curved portion 52 of the sleeve 28 and optical fiber 12 is fashioned with a permanent bend or curve. With the sleeve free end 46 oriented vertically, the preformed curved portion 52 facilitates a greater portion of the optical fiber 12 and sleeve 28 to be positioned prone. Consequently, a greater portion of the instrument's weight and ultimately the torque or shear generated from the weight is directed away from the incision 54 and the eye 56, thus reducing risks of surgical complications and undue stress on the eye 56 during surgery.

In a preferred embodiment of the present invention, the permanent bend or curve of the preformed curved portion 52 includes an at least substantially permanent bend or curve of the preformed curved portion 52 that is bent at an angle of up 180°, and more preferably at an angle of from about 1° to 180°.

The preformed curved portion 52 is fashioned by bending the sleeve 28 and the optical fiber 12 and subjecting the curved portion 52 to heat (e.g., exposure to boiling water or heated air) for a sufficient time depending on the heat temperature without adversely affecting the physical integrity of the sleeve 28 or the optical fiber 12. For boiling water, the optical fiber 12 and sleeve 28 is dipped into boiling water for about 5 seconds, and removed from the water for allowing the curved portion 52 to cool to room temperature through exposure to cool air flow or allowing it to rest in ambient temperature. Preferably, the forming process is implemented with the optical fiber 12 in a retracted position via the handpiece 26, and repeated with the optical fiber extended via the handpiece 26. Alternatively, the preformed curved portion 52 can be fashioned using a heated forming tool.

In one embodiment, the curved portion 52 is placed in a forming piece or tray that is configured to hold the curved portion 52 in a curved position. A heat gun is set to approximately 230° F. The heat gun is then placed approximately 0.5" from the curved portion 52 and heat is applied for approximately 30 seconds. This process can be performed multiple times until the curved configuration is set for the curved portion 52. The curved portion 52 is preferably allowed to stand for 15 minutes between heating intervals.

Figure 4:
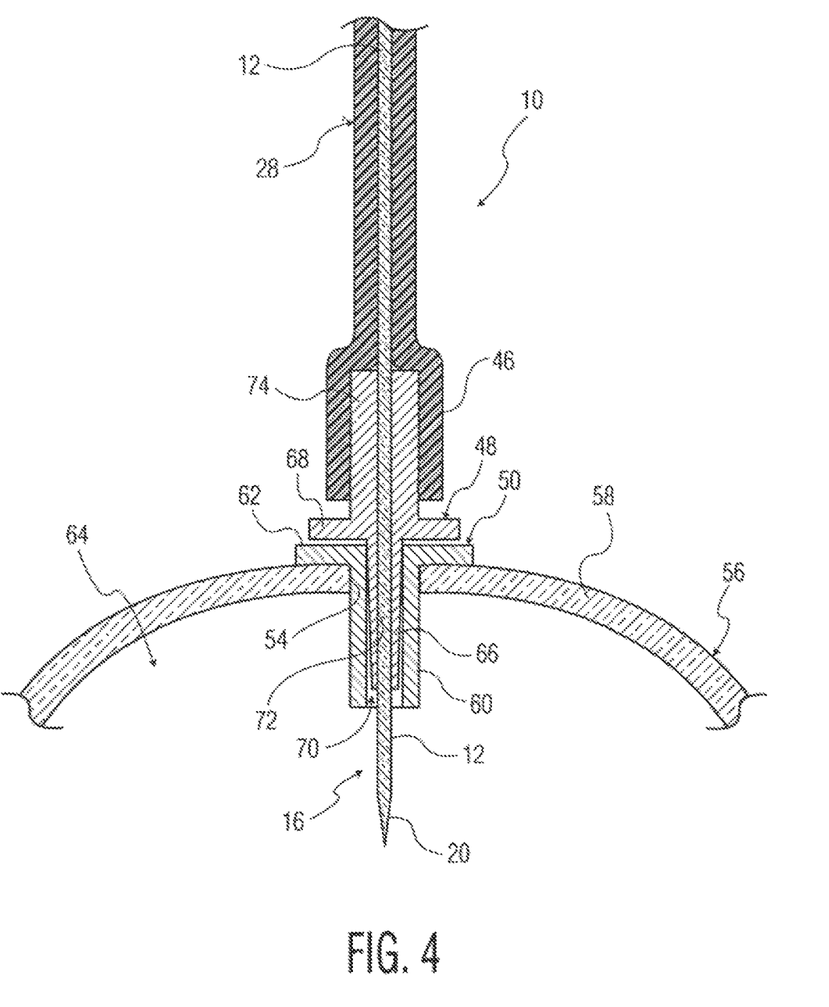
FIG. 4 is a detailed cross-sectional view of a tubular fitting of the microsurgical instrument securely coupled to a cannula implanted in the patient's eye and facilitating passage of an optical fiber therethrough in accordance with the present invention.

As previously described herein, the instrument 10 further includes a tubular fitting 48 disposed at the sleeve free end 46. The tubular fitting 48 is configured for expediting rigid coupling of the instrument 10 to a cannula 50 implanted in the sclera 58 of the eye 56 (see FIG. 4). The tubular fitting 48 includes a male taper portion 66 and a flange 68 extending therearound. The tubular fitting 48 can be fabricated from a machined metal (e.g., titanium) or a plastic polymer material. The male taper portion 66 is configured for connecting to a corresponding mating female part of the cannula 50 in frictional engagement therebetween to yield a rigid coupling joint as will be described hereinafter. In one embodiment, the male taper portion 66 is formed from stainless steel. In one embodiment, the male taper portion 66 is a 23 gauge tube. In another embedment, the male taper portion 66 is a 25 gauge tube. In another embodiment, shown in FIGS. 6A and 6B, the tubular fitting 48' does not include the winged flange 68 arrangement as shown in FIG. 4. As shown in FIGS. 6A and 6B, the tubular fitting 48' has a tapered profile from a cylindrical member 74' down to a male taper portion 66'.

The cannula 50 includes a tubular body portion 60 open at both ends, and a shoulder or flange 62 extending along an upper end thereof. The body portion 60 is implanted vertically through sclera 58 via an incision 54 made in the patient's eye 56. The flange 62 operates as a stop to limit the depth of the insertion of the cannula 50. The cannula 50 is introduced through the sclera 58 of the eye 56 via a trocar needle (not shown). During coupling between the tubular fitting 48 and cannula 50, the light emitting portion 20 located at the optical fiber distal end 16 projects from the male taper portion 66 of the tubular fitting 48 and into the vitreous chamber 64 of the patient's eye 56 by way of the cannula 50.

With reference to FIG. 4, there is shown a cross-sectional view of the tubular fitting 48 securely coupled to the cannula 50 implanted in the sclera 58 in the patient's eye 56 with the light emitting portion 20 of the optical fiber 12 extending into the vitreous chamber 64. The tubular fitting 48 and cannula 50 coupling enhances attachment of the instrument 10 to the patient's eye 56 in a secure manner, thus greatly reducing the likelihood of inadvertent withdrawal or displacement of the instrument 10 from the eye 56. Further, the tubular fitting 48 can be removed or disconnected from the cannula 50 by the surgeon. This feature allows the surgeon to readily swap instruments in a rapid manner with little or no difficulty.

As shown best in FIG. 4, the tubular body portion 60 of cannula 50 is inserted into the incision 54 of the patient's eye 56, and frictional retained in position by the sclera 58. It is noted that the exterior of the tubular body portion 60 may be provided with a textured surface area for enhancing frictional engagement with the tissue of the sclera 58. The cannula flange 62 operates as a stop abutting against the eye 56 and limiting the insertion depth of the tubular body portion 60 into the vitreous chamber 64.

The male taper portion 66 of the tubular fitting 48 is configured for insertion into a throughbore 70 of the cannula 50. The male taper portion 66 has a conically tapered profile which narrows gradually from the fitting flange 68 to the distal end thereof. The outer diameter of the taper portion 66 near the fitting flange 68 is greater than the inner diameter of the cannula throughbore 70 for providing a snug friction fit therebetween. It is noted that the form of the coupling between the tubular fitting 48 and the cannula 50 is not limited to the configuration and type shown and described herein, and that the present invention is intended to encompass any form of reversible couplings as known to one skilled in the art.

The tubular fitting 48 includes a cylindrical member 74 located opposite from the male taper portion 66, and a continuous through cavity 72 defined by the cylindrical member 74 and the male taper portion 66. The cylindrical member 74 is disposed within the distal end 46 of the sleeve 28 with the optical fiber 12 extending into the through cavity 72 of the tubular fitting 48. The tubular fitting 48 is secured to the sleeve 28 by adherence between the outer surface of the cylindrical member 74 and the inner surface of the sleeve distal end 46 via a suitable means including press fit engagement or adhesive such as, for example, acrylic polymers or cyanoacrylate. The light emitting portion 20 of the optical fiber 12 is inserted into the eye 56 as the tubular fitting 48 matingly engages the cannula 50. The light emitting portion 20 can be moved axially to a desired location within the eye 56 through operation of the finger knob 38 of the handpiece 26 to extend or retract the optical fiber 12 accordingly.

Figure 5:
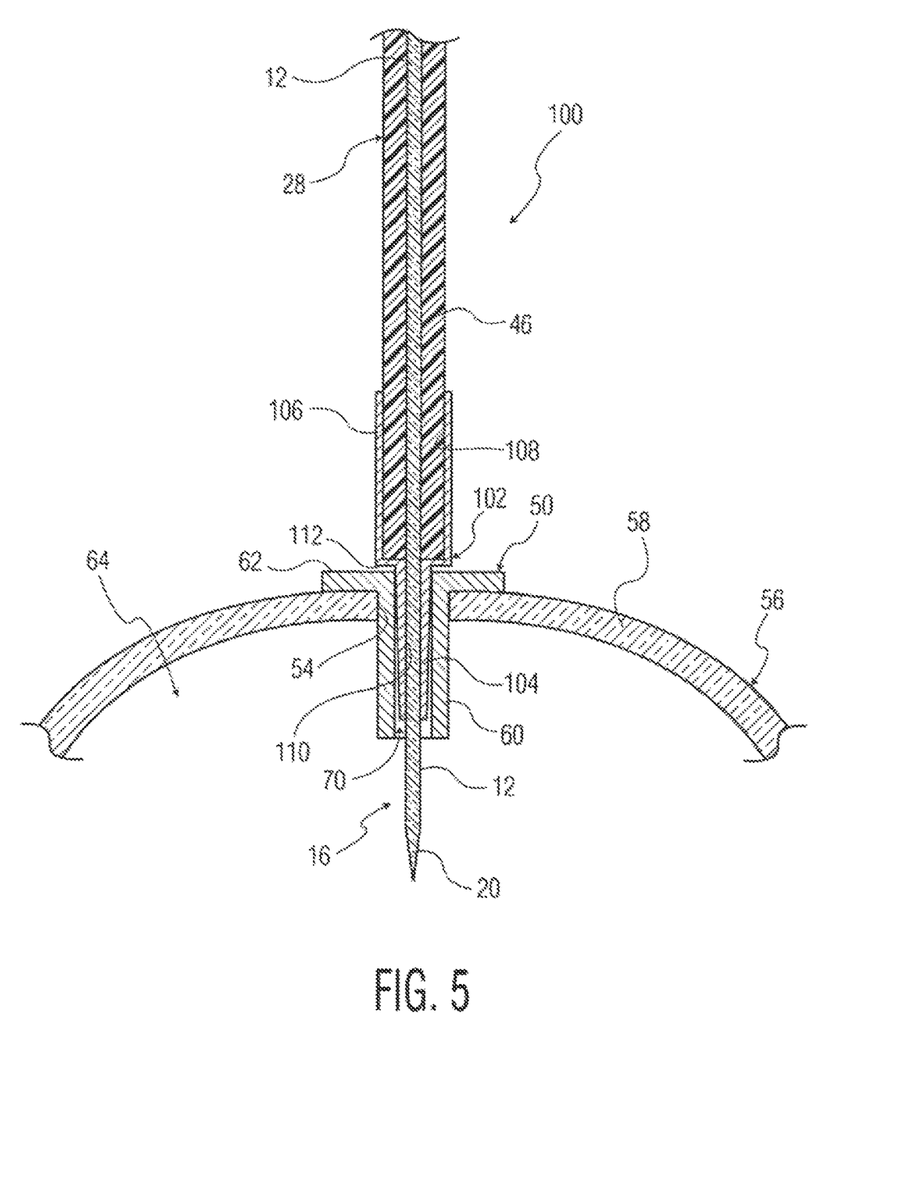
FIG. 5 is a detailed cross-sectional view of a tubular fitting of the microsurgical instrument securely coupled to a cannula implanted in the patient's eye and facilitating passage of an optical fiber therethrough in accordance with another embodiment of the present invention.

Referring to FIG. 5, there is shown a microsurgical instrument 100 for another embodiment of the present invention. The instrument 100 is similar in nearly all features as the previous embodiment. The instrument 100 includes a tubular fitting 102 having a different structural configuration from the previous embodiment. The tubular fitting 102 includes a male taper portion 104 located at one end thereof, and a cylindrical member 106 located at the other opposed end thereof. The cylindrical member 106 defines an interior cavity 108 suitably dimensioned for receiving and captively retaining the distal end 46 of the sleeve 28 and optical fiber 12 assembly therein via suitable means (e.g., adhesive retention). The extended portion of the optical fiber 12 passes through a through cavity 110 defined by the male tapered portion 104 of the tubular fitting 102.

Similar to the previous embodiment of the present invention, the male taper portion 104 of the tubular fitting 102 is configured for insertion into the through bore 70 of the cannula 50. The male taper portion 104 has a conically tapered profile which narrows gradually from a midportion region 112 to the distal end thereof. It is noted that the configuration, dimensions, and/or shape of the tubular fitting 102 is not limited to those disclosed herein and may be modified to yield other configurations, dimensions or shapes as necessary depending on the specific application, materials, cost factors, fabrication methods, coupling design, and the like.

Embodiments List

The following list includes particular embodiments of the present invention. But the list is not limiting and does not exclude embodiments otherwise described or alternate embodiments, as would be appreciated by one of ordinary skill in the art.

1. A microsurgical instrument for illuminating an interior site, comprising:
an optical fiber having a length between opposed proximal and distal ends, said proximal end of the optical fiber being configured for operative engagement with an illumination light source; said distal end of the optical fiber including a light emitting portion; and a preformed curved portion of the optical fiber proximate to the distal end, said curved portion having a predetermined bend or curve.

2. The instrument of embodiment 1, wherein the curved portion of the optical fiber is bent to an angle of up to 180°.

3. The instrument of any one or more of embodiments 1-2, further comprising: a handpiece having a bore extending therethrough; said optical fiber extending through the handpiece bore; and an adjustable mechanism operatively associated with the handpiece, said adjustable mechanism operatively engaged to the optical fiber for selectively moving said optical fiber backward and forward relative to said handpiece bore.

4. The instrument of any one or more of embodiments 1-3, further comprising a flexible tubular sleeve enclosing at least a portion of the optical fiber, said tubular sleeve having a preformed curved portion corresponding to the curved portion of the optical fiber.

5. The instrument of any one or more of embodiments 1-4, further comprising a tubular fitting affixed to a distal end of the sleeve through which the distal end of the optical fiber passes therethrough, said tubular fitting being configured for coupling engagement with a cannula to rigidly secure the two together.

6. The instrument of any one or more of embodiments 1-5, wherein the tubular fitting comprises a tapered portion extending therefrom for insertion into a throughbore of the cannula for frictional retainment therein.

7. The instrument of any one or more of embodiments 1-6, wherein the tubular fitting is composed of a material selected from the group consisting of a metal material, a ceramic material, a plastic polymer material and combinations thereof.

8. The instrument of any one or more of embodiments 1-7, wherein the light emitting portion of the optical fiber includes a member selected from the group consisting of a cone shaped taper and a cylinder shaped square end.

9. A microsurgical instrument for illuminating an interior site, comprising: an optical fiber having a length between opposed proximal and distal ends, said proximal end of the optical fiber being configured for operative engagement with an illumination light source; said distal end of the optical fiber including a light emitting portion; a flexible tubular sleeve enclosing at least a portion of the optical fiber; and a tubular fitting affixed to a distal end of the sleeve through which the distal end of the optical fiber passes therethrough, said tubular fitting being configured for coupling engagement with a cannula to rigidly secure the two together.

10. The instrument of embodiment 9, further comprising a preformed curved portion of the optical fiber within said sleeve proximate to the distal end, said curved portion having a predetermined bend or curve.

11. The instrument of any one or more of embodiments 9-10, further comprising: a handpiece having a bore extending therethrough; said optical fiber extending through the handpiece bore; and an adjustable mechanism operatively associated with the handpiece, said adjustable mechanism operatively engaged to the optical fiber for selectively moving said optical fiber backward and forward relative to said handpiece bore to control the length of extension thereof from said tubular fitting.

12. The instrument of any one or more of embodiments 9-11, wherein the tubular fitting comprises a tapered portion extending therefrom for insertion into a throughbore of the cannula for frictional retainment therein.

13. The instrument of any one or more of embodiments 9-12, wherein the tubular fitting is composed of a material selected from the group consisting of a metal material, a ceramic material, a plastic polymer material and combinations thereof.

14. The instrument of any one or more of embodiments 9-14, wherein the light emitting portion of the optical fiber includes a member selected from the group consisting of a cone shaped taper and a cylinder shaped square end.

15. A microsurgical instrument for illuminating an interior site, comprising: an optical fiber having a length between opposed proximal and distal ends, said proximal end of the optical fiber being configured for operative engagement with an illumination light source; said distal end of the optical fiber including a light emitting portion; a preformed curved portion of the optical fiber proximate to the distal end, said curved portion having a predetermined bend or curve; a flexible tubular sleeve enclosing at least a portion of the optical fiber, said tubular sleeve having a preformed curved portion for maintaining the curved portion of the optical fiber; and a tubular fitting affixed to a distal end of the sleeve through which the distal end of the optical fiber passes therethrough, said tubular fitting being configured for coupling engagement within an interior portion of said cannula, thereby rigidly securing the two together.

16. The instrument of embodiments 15, wherein the curved portion of the optical fiber is bent to an angle of up to 180°.

17. The instrument of any one or more of embodiments 15-16, further comprising: a handpiece having a bore extending therethrough; said optical fiber extending through the handpiece bore; and an adjustable mechanism operatively associated with the handpiece, said adjustable mechanism operatively engaged to the optical fiber for selectively moving said optical fiber backward and forward relative to said handpiece bore to control the length of extension thereof from said tubular fitting.

18. The instrument of any one or more of embodiments 15-17, wherein the tubular fitting comprises a tapered portion extending therefrom for insertion into a throughbore of the cannula for frictional retainment therein.

19. The instrument of any one or more of embodiments 15-18, wherein the tubular fitting is composed of a material selected from the group consisting of a metal material, a ceramic material, a plastic polymer material and combinations thereof.

20. The instrument of any one or more of embodiments 15-19, wherein the light emitting portion of the optical fiber includes a member selected from the group consisting of a cone shaped taper and a cylinder shaped square end.

Further embodiments herein may be formed by supplementing an embodiment with one or more element from any one or more other embodiment herein, and/or substituting one or more element from one embodiment with one or more element from one or more other embodiment herein.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A microsurgical instrument for illuminating an interior site, comprising:
   an optical fiber having a length between opposed proximal and distal ends, said proximal end of the optical fiber being configured for operative engagement with an illumination light source;
   said distal end of the optical fiber including a light emitting portion;
   a preformed curved portion of the optical fiber proximate to the distal end, said curved portion having a predetermined bend or curve;
   a flexible tubular sleeve enclosing at least a portion of the optical fiber; and
   a tubular fitting including a first end portion having a first outer diameter, the first end portion affixed to a distal end of the flexible tubular sleeve, and a second end portion having a second outer diameter that is smaller than the first outer diameter, the second end portion being configured to affix the tubular fitting to a cannula.

2. The instrument of claim 1, wherein the curved portion of the optical fiber is bent to an angle of up to 180°.

3. The instrument of claim 1, further comprising:
   a handpiece having a bore extending therethrough;
   said optical fiber extending through the handpiece bore; and
   an adjustable mechanism operatively associated with the handpiece, said adjustable mechanism operatively engaged to the optical fiber for selectively moving said optical fiber backward and forward relative to said handpiece bore.

4. The instrument of claim 3, wherein the optical fiber is positioned by the adjustable mechanism in either a retracted position or an extended position with respect to the tubular fitting.

5. The instrument of claim 4, wherein the optical fiber extends between 0.015" to 0.055" from the tubular fitting in the retracted position.

6. The instrument of claim 4, wherein the optical fiber extends 0.035" from the tubular fitting in the retracted position.

7. The instrument of claim 4, wherein the optical fiber extends between 0.20" to 0.45" from the tubular fitting in the extended position.

8. The instrument of claim 4, wherein the optical fiber extends 0.285" from the tubular fitting in the extended position.

9. The instrument of claim 4, wherein the optical fiber extends 1.25" from the tubular fitting in the extended position.

10. The instrument of claim 1, wherein said tubular sleeve has a preformed curved portion corresponding to the curved portion of the optical fiber.

11. The instrument of claim 1, wherein the light emitting portion of the optical fiber includes a member selected from the group consisting of a cone shaped taper and a cylinder shaped end.

12. A microsurgical instrument for illuminating an interior site, comprising:
- an optical fiber having a length between opposed proximal and distal ends, said proximal end of the optical fiber being configured for operative engagement with an illumination light source;
- said distal end of the optical fiber including a light emitting portion;
- a handpiece having a bore extending therethrough;
- said optical fiber extending through the handpiece bore;
- an adjustable mechanism operatively associated with the handpiece, said adjustable mechanism operatively engaged to the optical fiber for selectively moving said optical fiber backward and forward relative to said handpiece bore;
- a flexible tubular sleeve enclosing at least a portion of the optical fiber; and
- a tubular fitting including a first end portion having a first outer diameter, the first end portion affixed to a distal end of the flexible tubular sleeve, and a second end portion having a second outer diameter that is smaller than the first outer diameter, the second end portion being configured to affix the tubular fitting to a cannula;
- wherein the optical fiber is positioned by the adjustable mechanism in either a retracted position or an extended position with respect to the tubular fitting, and the optical fiber extends a maximum of 1.25" from the tubular fitting in the extended position.

13. The instrument of claim 12, wherein the optical fiber extends between 0.015" to 0.055" from the tubular fitting in the retracted position.

14. The instrument of claim 12, wherein the optical fiber extends 0.035" from the tubular fitting in the retracted position.

15. A microsurgical instrument for illuminating an interior site, comprising:
- an optical fiber having a length between opposed proximal and distal ends, said proximal end of the optical fiber being configured for operative engagement with an illumination light source;
- said distal end of the optical fiber including a light emitting portion;
- a preformed curved portion of the optical fiber proximate to the distal end, said curved portion having a predetermined bend or curve;
- a flexible tubular sleeve enclosing at least a portion of the optical fiber; and
- a tubular fitting including a first end portion having a first outer diameter, the first end portion affixed to a distal end of the flexible tubular sleeve, and a second end portion having a second outer diameter that is smaller than the first outer diameter, the second end portion being configured to fix the tubular fitting in a stationary position.

16. The instrument of claim 15, wherein the curved portion of the optical fiber is bent to an angle of up to 180°.

17. The instrument of claim 15, wherein said tubular sleeve has a preformed curved portion corresponding to the curved portion of the optical fiber.

18. The instrument of claim 15, wherein the light emitting portion of the optical fiber includes a member selected from the group consisting of a cone shaped taper and a cylinder shaped end.

* * * * *